(12) United States Patent
White et al.

(10) Patent No.: US 11,937,032 B2
(45) Date of Patent: *Mar. 19, 2024

(54) SYSTEM FOR WIRELESS RETRIEVAL OF MEASURED COMPONENT DATA

(71) Applicant: Black & Decker Inc., New Britain, CT (US)

(72) Inventors: Daniel J. White, Baltimore, MD (US); Matthew J. Velderman, Baltimore, MD (US); Andrew E. Seman, Pylesville, MD (US); Christopher W. Lemieux, Mount Airy, MD (US); Gary Hill, Red Lion, PA (US)

(73) Assignee: BLACK & DECKER INC., New Britain, CT (US)

( * ) Notice: Subject to any disclaimer, the term of this patent is extended or adjusted under 35 U.S.C. 154(b) by 57 days.

This patent is subject to a terminal disclaimer.

(21) Appl. No.: 17/655,315

(22) Filed: Mar. 17, 2022

(65) Prior Publication Data

US 2022/0210526 A1 Jun. 30, 2022

Related U.S. Application Data

(63) Continuation of application No. 17/125,036, filed on Dec. 17, 2020, now Pat. No. 11,363,356, which is a (Continued)

(51) Int. Cl.
*H04Q 9/00* (2006.01)
*F16B 31/02* (2006.01)
(Continued)

(52) U.S. Cl.
CPC ............ *H04Q 9/00* (2013.01); *F16B 31/028* (2013.01); *G01D 11/30* (2013.01); *G01D 21/00* (2013.01);
(Continued)

(58) Field of Classification Search
CPC .... H04Q 9/00; H04Q 2209/43; F16B 31/028; F16B 13/0858; G01D 11/30; G01D 21/00; G01L 5/00; G01N 33/383
See application file for complete search history.

(56) References Cited

U.S. PATENT DOCUMENTS 3,332,312 A * 7/1967 Bixby ................. F16B 13/0858
411/15
6,285,283 B1 * 9/2001 Rand .................. G08B 13/1463
340/568.4
(Continued)

FOREIGN PATENT DOCUMENTS

| DE | 102010001144 A | | 7/2011 |
|---|---|---|---|
| JP | 2011184994 A | * | 9/2011 |
| WO | 2011090539 A | | 7/2011 |

*Primary Examiner* — James J Yang
(74) *Attorney, Agent, or Firm* — Kofi A. Schulterbrandt

(57) ABSTRACT

A system for remotely retrieving sensed conditions at one or more building components. The building components are remote or numerous so that a wireless collection of the sensed conditions provides a significant benefit to a builder or building operator. A remote transceiver sends a wireless signal to a building component. The building component includes an onboard transceiver. At least some of the energy from the transmitted wireless signal is received by the onboard transceiver, sent to a storage device, and stored therein. The stored energy is used to operate a sensor for sensing an onboard condition. The onboard condition is then wirelessly transmitted by the onboard transceiver back to the remote transceiver to be displayed.

17 Claims, 10 Drawing Sheets

Related U.S. Application Data continuation of application No. 15/840,176, filed on Dec. 13, 2017, now Pat. No. 10,904,644.

(60) Provisional application No. 62/456,243, filed on Feb. 8, 2017, provisional application No. 62/438,639, filed on Dec. 23, 2016.

(51) Int. Cl.
*G01D 11/30* (2006.01)
*G01D 21/00* (2006.01)
*G01L 5/00* (2006.01)
*G01N 33/38* (2006.01)
*F16B 13/08* (2006.01)

(52) U.S. Cl.
CPC ............. *G01L 5/00* (2013.01); *G01N 33/383* (2013.01); *F16B 13/0858* (2013.01); *H04Q 2209/43* (2013.01)

(56) References Cited

U.S. PATENT DOCUMENTS

| | | | |
|---|---|---|---|
| 7,412,898 B1 * | 8/2008 | Smith | F16B 31/025 |
| | | | 73/761 |
| 9,483,674 B1 | 11/2016 | Fink et al. | |
| 2008/0253858 A1 | 10/2008 | Hsieh | |
| 2008/0278319 A1 | 11/2008 | Meiksin et al. | |
| 2010/0054891 A1 | 3/2010 | Nishida et al. | |
| 2011/0181393 A1 | 7/2011 | Tillotson et al. | |
| 2011/0248825 A1 * | 10/2011 | Hamel | H04Q 9/00 |
| | | | 340/10.1 |
| 2013/0186951 A1 | 7/2013 | Zhu et al. | |
| 2017/0102304 A1 | 4/2017 | Saleem | |

* cited by examiner

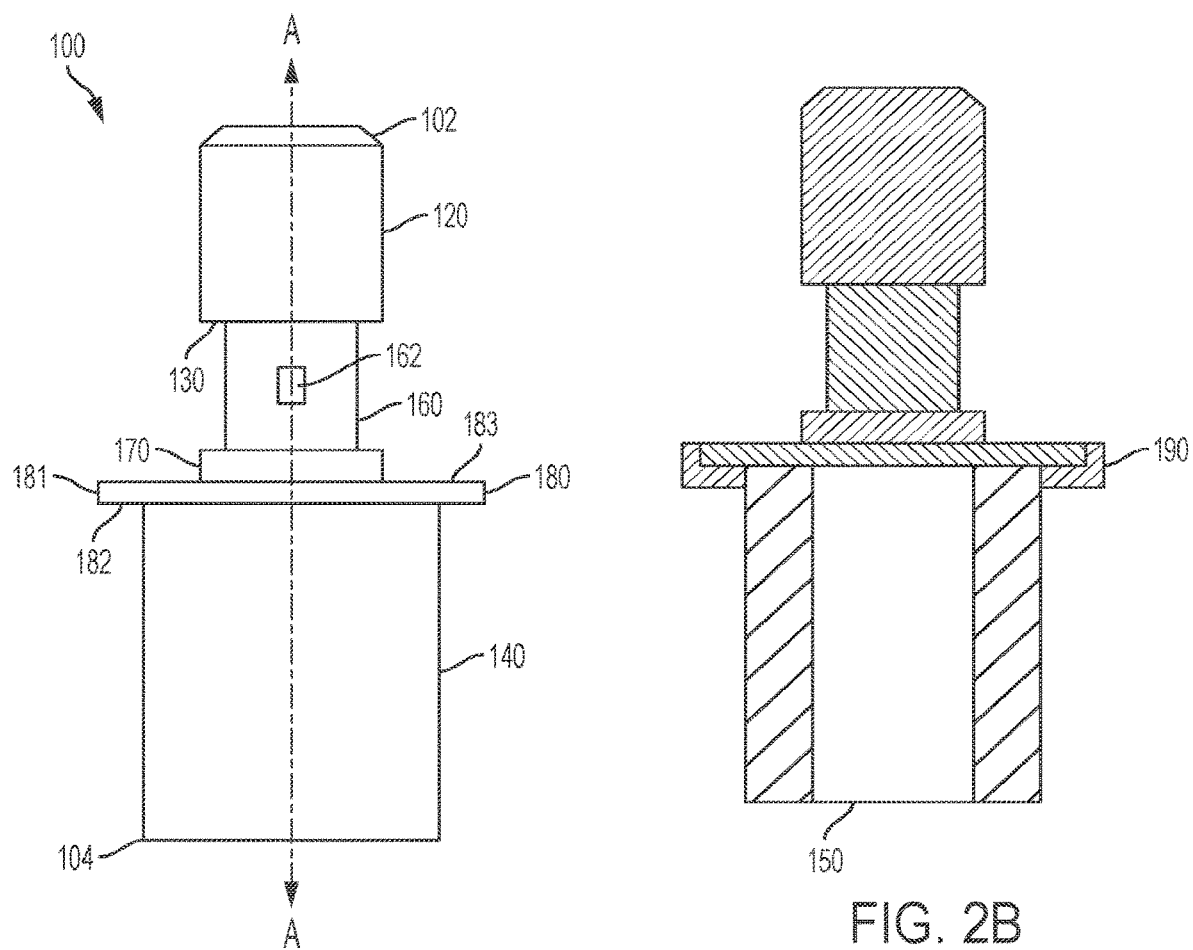
FIG. 2A
FIG. 2B
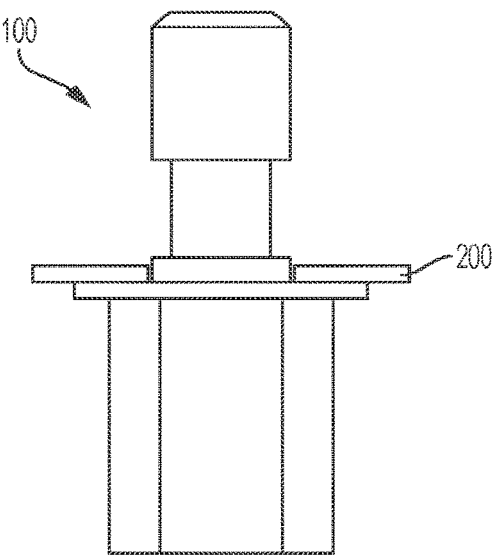
FIG. 2C

SYSTEM FOR WIRELESS RETRIEVAL OF MEASURED COMPONENT DATA

CROSS-REFERENCE TO RELATED APPLICATIONS

This is a continuation of U.S. application Ser. No. 17/125,036, filed Dec. 17, 2020 which is a continuation of U.S. application Ser. No. 15/840,176, filed Dec. 13, 2017 which claims priority of U.S. Provisional Application 62/438,639 filed Dec. 23, 2016, and U.S. Provisional Application 62/456,243 filed Feb. 8, 2017, and the disclosures of which are incorporated herein by reference in their entirety.

BACKGROUND OF THE INVENTION

In certain environments (e.g., a space station, a building or construction site, a warehouse, a storage yard, etc.) it would be desirable to know/confirm the existence of and/or a condition (e.g., a physical condition) at a particular location in the environment. Furthermore, as certain locations may be numerous or inaccessible, it might be most convenient if the condition at the particular location could be retrieved or gathered by a user wirelessly when the location is a remote distance from the user. For example, in a building or construction site it might be desirable to know the load being borne by a particular load bearing member. With respect to the borne load, a building inspector or designer might like to remotely gather information about one or more members (e.g., load bearing anchors) in order to confirm that such members are being loaded within code permitted parameters\limits. Alternatively, during construction of a building, a contractor might desire to wirelessly collect information regarding the presence or identity of certain members and a condition (e.g., how much load those members are bearing or if moisture is present) under which they exist in their various locations. A designer (e.g., a structural designer) might even find that he/she is able to design more efficiently and less conservatively knowing that an exact or close to exact condition (e.g., load being borne by) of the member can be determined. The present invention to be described below includes a system for wirelessly retrieving information about a sensed condition (including the fact of existence of the physical object about which the condition is being sought) at a remote location. For example, when the retrieval system retrieves information about the existence of elements, the retrieved information can be used to determine installation progress during construction.

SUMMARY OF THE INVENTION

The system for wirelessly retrieving information about a sensed condition at a remote location includes an onboard station at the location and a RFID transceiver remote from the location. The onboard station includes an onboard RFID transceiver capable of receiving a wireless signal from the remote RFID transceiver, a sensor for sensing the condition at the location and an energy storage device for powering the sensor. Each of the onboard RFID transceiver, the sensor, and the energy storage device are in electrical communication with each other. An LED may also be included in the onboard station. The LED would be energizable to visually communicate information about the existence of the system or the sensed condition. The electrical communication is such that the onboard RFID transceiver receives energy via the wireless signal transmitted from the remote RFID transceiver. The energy storage device receives at least some of the energy received at the onboard RFID transceiver and stores at least some of that energy. The sensor receives and uses at least some of the stored energy in order to sense the condition. The sensor generates a first signal representing a value of the condition. The onboard RFID transceiver receives the first signal and transmits a second wireless signal which is received by the remote RFID transceiver.

In one embodiment the present invention discloses a system for wirelessly retrieving a sensed condition at a remote location and which includes: (1 a remote transceiver capable of receiving a sensed condition; 2) a building component including; (3 an onboard transceiver capable of sending and receiving a sensed condition; (4 an energy storage device; and (5 a sensor for sensing a condition at the remote location; wherein the onboard transceiver, the storage device, and the sensor communicate electrically with each other, wherein the onboard transceiver is capable of receiving a wireless signal from the remote transceiver, wherein energy from the wireless signal is received and stored in the energy storage device, wherein the sensor uses a portion of the stored energy from the energy storage device to sense a condition at the remote location, the sensor generates a first signal related to the sensed condition, and the sensor sends the first signal to the onboard transceiver, and wherein the onboard transceiver transmits a second wireless signal related to the sensed condition back to the remote transceiver.

In another embodiment the present invention discloses a connector for wirelessly retrieving a sensed condition at a remote location, the connector for connection to a concrete anchor, the concrete anchor for securement in concrete and including a first locking member for locking connection with the connector, the connector including: (1 a connector body including a first end and a second end, the first end including a second locking member for locking connection with the first locking member, the second end including a third locking member for receiving an object to be anchored to the concrete; (2 an onboard transceiver capable of sending and receiving a sensed condition; 3) an energy storage device; (4 a sensor for sensing a condition at the remote location; wherein the onboard transceiver, the storage device, and the sensor communicate electrically with each other, wherein the onboard transceiver receives a wireless signal; wherein energy from the wireless signal is received and stored in the energy storage device, wherein the sensor uses a portion of the stored energy from the energy storage device to sense a condition at the remote location, the sensor generates a first signal related to the sensed condition, and the sensor sends the first signal to the onboard transceiver, and wherein the onboard transceiver transmits a second wireless signal related to the sensed condition.

In another embodiment the present invention discloses a concrete anchor for wirelessly retrieving a sensed condition at a remote location, the concrete anchor for securement in concrete, the anchor including: (1 an anchor body including a first end and a second end, the second end including a locking member for facilitating locking connection with an object to be secured to the concrete; (2 an onboard transceiver capable of sending and receiving a sensed condition; (3 an energy storage device; and (4 a sensor for sensing a condition at the remote location; wherein the onboard transceiver, the storage device, and the sensor communicate electrically with each other, wherein the onboard transceiver receives a wireless signal; wherein energy from the wireless signal is received and stored in the energy storage device, wherein the sensor uses a portion of the stored energy from the energy storage device to sense a condition at the remote location, the sensor generates a first signal related to the sensed condition, and the sensor sends the first signal to the onboard transceiver, and wherein the onboard transceiver transmits a second wireless signal related to the sensed condition.

In another embodiment the present invention discloses (in combination) a concrete anchor and a connector for wirelessly retrieving a sensed condition at a remote location including: (1 a concrete anchor for securement in concrete, the concrete anchor including a first end and a second end, the second end including a first locking member; (2 a connector including a first end and a second end, the first end including a second locking member for locking connection with the first locking member of the concrete anchor, the second end including a third locking member for lockingly receiving an object to be anchored to the concrete; (3 an onboard transceiver capable of sending and receiving a sensed condition; (4 an energy storage device; and (5 a sensor for sensing a condition at the remote location; wherein the onboard transceiver, the storage device, and the sensor communicate electrically with each other, wherein the onboard transceiver receives a wireless signal; wherein energy from the wireless signal is received and stored in the energy storage device, wherein the sensor uses a portion of the stored energy from the energy storage device to sense a condition at the remote location, the sensor generates a first signal related to the sensed condition, and the sensor sends the first signal to the onboard transceiver, and wherein the onboard transceiver transmits a second wireless signal related to the sensed condition.

DESCRIPTION OF THE DRAWINGS

Preferred embodiments of the invention will now be described, by way of example, with reference to the accompanying drawings, of which:

FIG. 2A shows an anchor connector of the present invention.

FIG. 2B shows a cross-sectional view of the anchor connector of FIG. 2A.

FIG. 2C shows a side view of the anchor connector of FIG. 2A further including a smart disk.

FIG. 2F shows a partial cross-sectional view of a drop-in anchor including a

DETAILED DESCRIPTION OF THE PREFERRED EMBODIMENTS

Figure 1A:
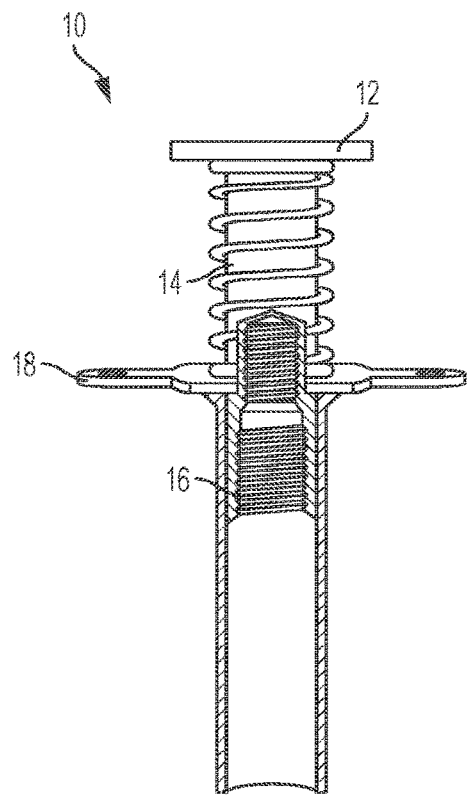
FIG. 1A shows a cross sectional view of a conventional bang-in concrete deck cast in place anchor.
Figure 1B:
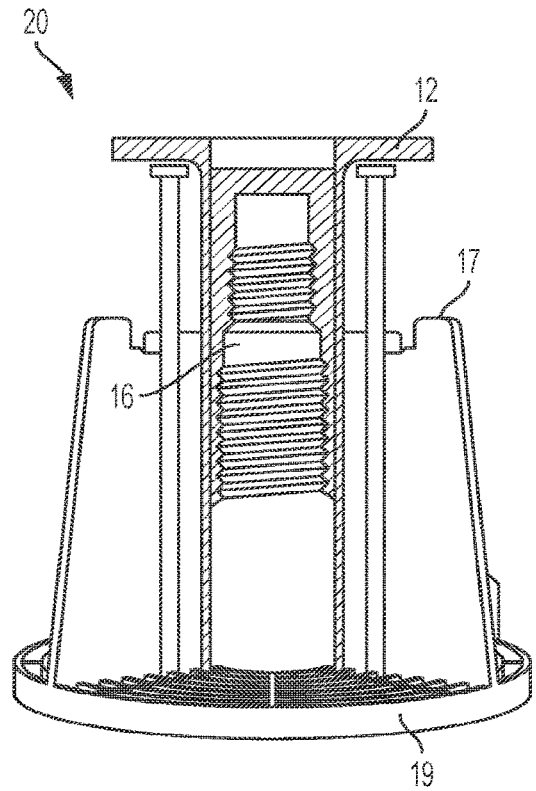
FIG. 1B shows a cross sectional view of a conventional wood form cast in place anchor.

FIGS. 1A and 1B show a conventional concrete decking precast anchor 10 and a conventional wood form precast anchor 20 respectively. Both anchors 10 and 20 include a shoulder 12 on a first end which extends radially outward so that when set in concrete it resists pull-out. The anchors also include female threads 16 on a second end for receiving a threaded support rod after installation. An intermediate portion 14 is disposed between shoulder 12 and threaded member 16. When set, both types of anchor are secured in the cured concrete with an exposed connector 16 (e.g., a female thread). The female thread 16 is now able to receive an object (e.g., a threaded hanger rod). The hanger rod may be secured to the concrete via the anchor at one end and to a building component at the other end. Building components to be secured to the concrete may include building conduit for supporting various building systems (e.g., fire, HVAC, electrical, etc.).

Figure 1C:
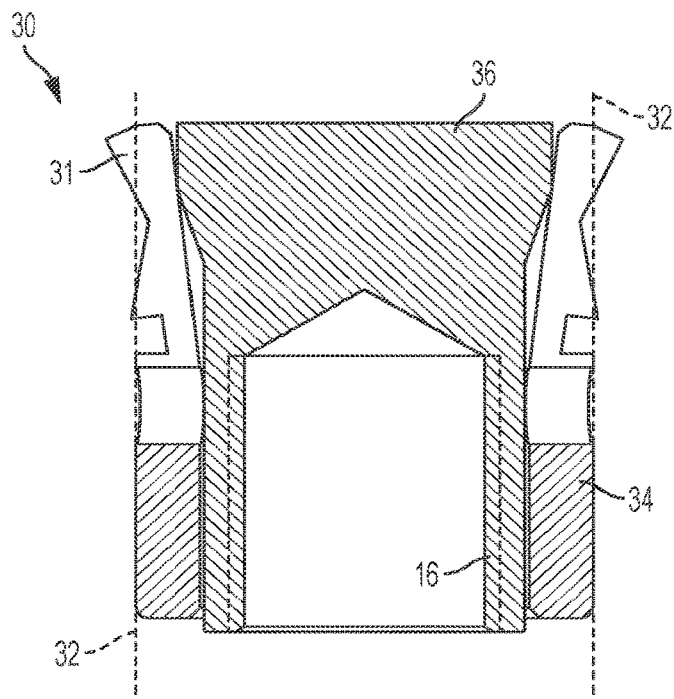
FIG. 1C shows a partial cross sectional view if a conventional drop in wedge impact plug anchor.
Figure 1D:
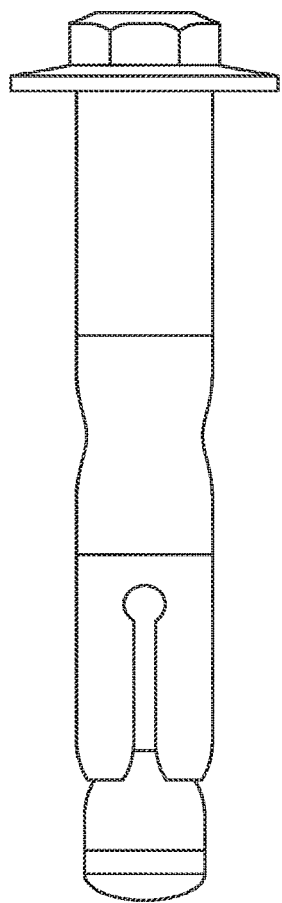
FIG. 1D shows a side view of a conventional threaded actuated wedge drop-in anchor.
Figure 1E:
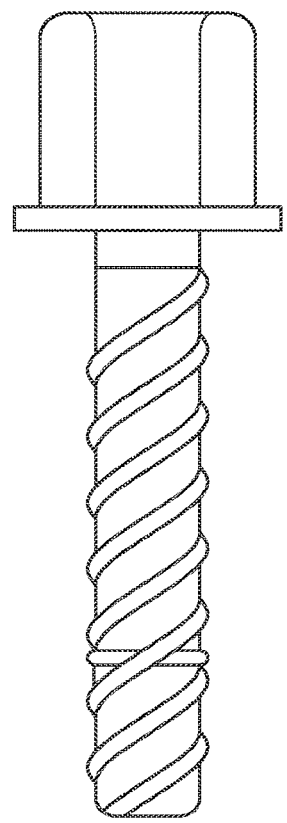
FIG. 1E shows a side view of a conventional threaded screw in concrete anchor.

In addition to the above mentioned cast in place anchors, the present invention relates to drop in anchors of the type shown in cross-section in FIG. 1C. A drop-in anchor 30 is placed after concrete setting. A hole 32 (e.g., cylindrical) is drilled in the concrete. Drop-in anchor 30 (e.g., cylindrical in shape) is then inserted into hole 32. The anchors usually include a well know wedge mechanism which when actuated, forces radially expandable portions 31 of the anchor outward into contact with the walls of the drilled concrete hole 32 to wedge anchor 30 into hole 32. Similar to the cast in place anchors 10, 20 described above, a connector (e.g., a threaded female connector) is exposed for connection to a support member (e.g., a threaded rod). Certain conventional features of the above types of concrete anchors are described in U.S. Pat. Nos. 6,240,697; 4,211,048; 5,593,261; 6,652,207 and 3,769,774, each of which is incorporated herein by reference in their entirety.

FIGS. 2A and 2B show a smart anchor connector or smart connector 100. Smart connector 100 includes a first end 102 and a second end 104 through which a central longitudinal axis A-A passes. At first end 102 of connector 100 is a threaded portion 120 (e.g., male thread) which can be threadably connected to the female connectors of the anchors 10, 20, 30 of FIG. 1. A lower portion of connector 120 may include a bearing surface 130. At second end 104 of connector 100 is a threaded female connector 150 shown in FIG. 2. Connector 100 includes a hollow cylinder 140 at a second 140. The wall surface forming the hollow portion of the cylinder is the same female threaded surface of as threaded connector 150. An intermediate portion 160 extends between threaded connectors 120 and 150. Also between threaded connectors 120 and 150 is a projection 180 (e.g., radial projection). Radial projection 180 can includes a center bearing 170 that shares a central axis with longitudinal axis A-A. Radial projection 180 also includes an outer edge 181, a top surface 183 and a bottom surface 182.

When threaded connector 120 of connector 100 is connected to the threaded female connector 16 of anchors 10, 20 or 30, threaded female connector 150 is exposed for receiving a threaded rod that would have otherwise been received by the female threaded openings in anchors 10, 20, and 30. Therefore, in operation connector 100 is positioned between and/or in series with anchors 10, 20, or 30 and the threaded support rod. When the threaded rod is connected directly to anchors 10, 20, or 30, load from the threaded rod is transferred from the rod to anchors 10, 20, or 30 and then to the concrete. On the other hand, when connector 100 is placed between anchors 10, 20, or 30 and the threaded rod, load (e.g., tension load) from the rod is transferred through smart connector 100 to anchors 10, 20, or 30 and then to the concrete.

Anchors 10, 20, 30 may also be redesigned so that after setting, female threads 16 are countersunk below the concrete surface. Such countersinking would allow a connector 100 to also be at least partially countersunk in the concrete if so desired. For example, anchor 20 may also include a bottom 19 against which anchor 20 rests on a wood form during and after installation, but before the wood form is stripped. Furthermore, anchor 20 includes a seat 17 on which shoulder 12 rests after shoulder 12 is impacted (e.g., by a hammer). The length of thread 16 and the pre-set distance between shoulder 12 and seat 17 may be adjusted such that after installation, threads 16 do not extend all the way to bottom 19. If threads 16 stop short of bottom 19 after installation, a void in the concrete is maintained between the thread and the surface of the concrete so that connector 100 may be received in the void and at least partially counter sunk in the concrete after attachment to anchor 20.

Smart connector 100 may include a sensor thereon for sensing a condition at the anchor (e.g., a physical condition, or load) that passes through the anchor. For example, that load may be measured by a strain gauge positioned on smart connector 100. The gauge may be positioned to measured strain/load at an intermediate portion 160 of connector 100 between the male threaded connector 120 and the female threaded connector 150. In one embodiment, it may be convenient to reduce the dimensions (e.g., radial or cross-sectional) of intermediate portion 160 with respect to threaded connectors 120, 150 in order to amplify or best sense the strain experienced by the intermediate portion and therefore the load being transferred through the system to the concrete. Therefore, after installation, an exact amount of load being transferred through anchors 10, 20, 30 can be determined and know. It should also be noted that in addition to a tensile strain, a compressive strain can also be the basis of a load calculation when a compressive load is induced in a portion of anchor 10, 20, or 30 or connector 100.

As discussed above, installed anchor systems frequently include components that are too remote or too numerous to easily collect the determined load information. Therefore, the present specification contemplates a wireless system for remotely retrieving actual anchor load information. FIG. 2C shows a washer or smart washer 200. Washer 200 can include the RFID transceiver, the sensor, and/or the storage device of the system of FIG. 3. When one of these elements is absent from washer 200, the element may be located on the anchor in proximity to washer 200 so that it can communicate electrically with washer 200. Smart washer 200 is disk or washer shaped but could take on any convenient form depending on the structure of the anchor on to which it is yoked or connected. FIG. 3 shows washer 200 including an inner wall surface 210 defining a washer inner diameter and an outer wall surface 210 having an outer washer diameter. Washer 200 may also includes a thickness of a dimension that is significantly less than the outer surface diameter. In one embodiment shown in FIG. 2C, washer 200 sits on a top support surface 183 of projection 180 and is radially secured by a center bearing 170. The location of washer 200 on surface 183 is in proximity to intermediate portion 160 so that washer 200 may receive an electrical signal from a strain gauge 162 located at intermediate portion 160.

Figure 2D:
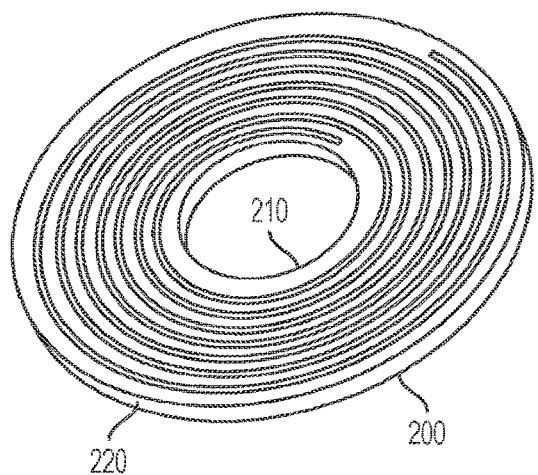
FIG. 2D shows a top perspective view of the smart disk of FIG. 2C.
Figure 2E:
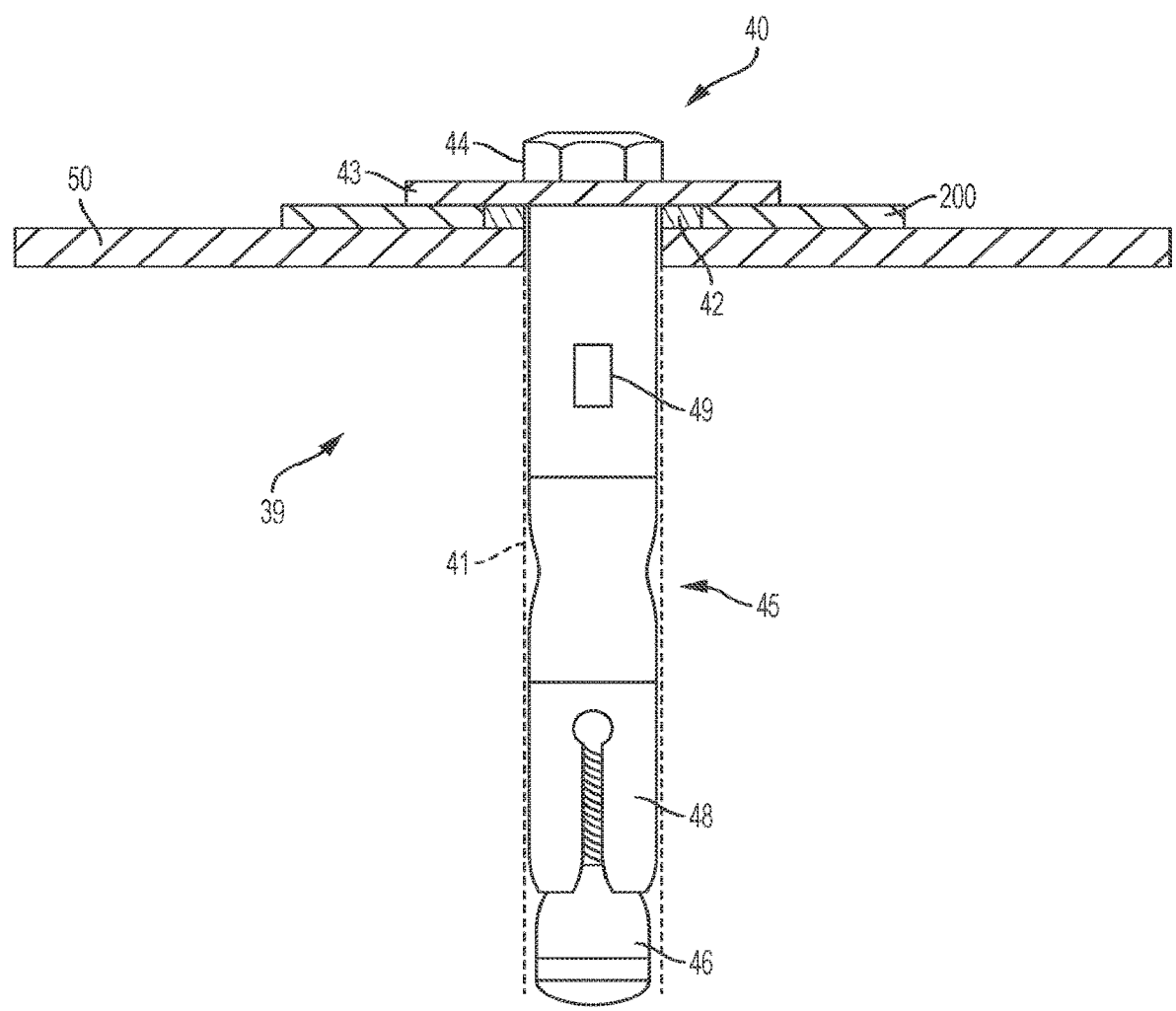
FIG. 2E shows a partial cross-sectional view of a drop-in anchor including a flange configuration for securing a smart disk.
Figure 2F:
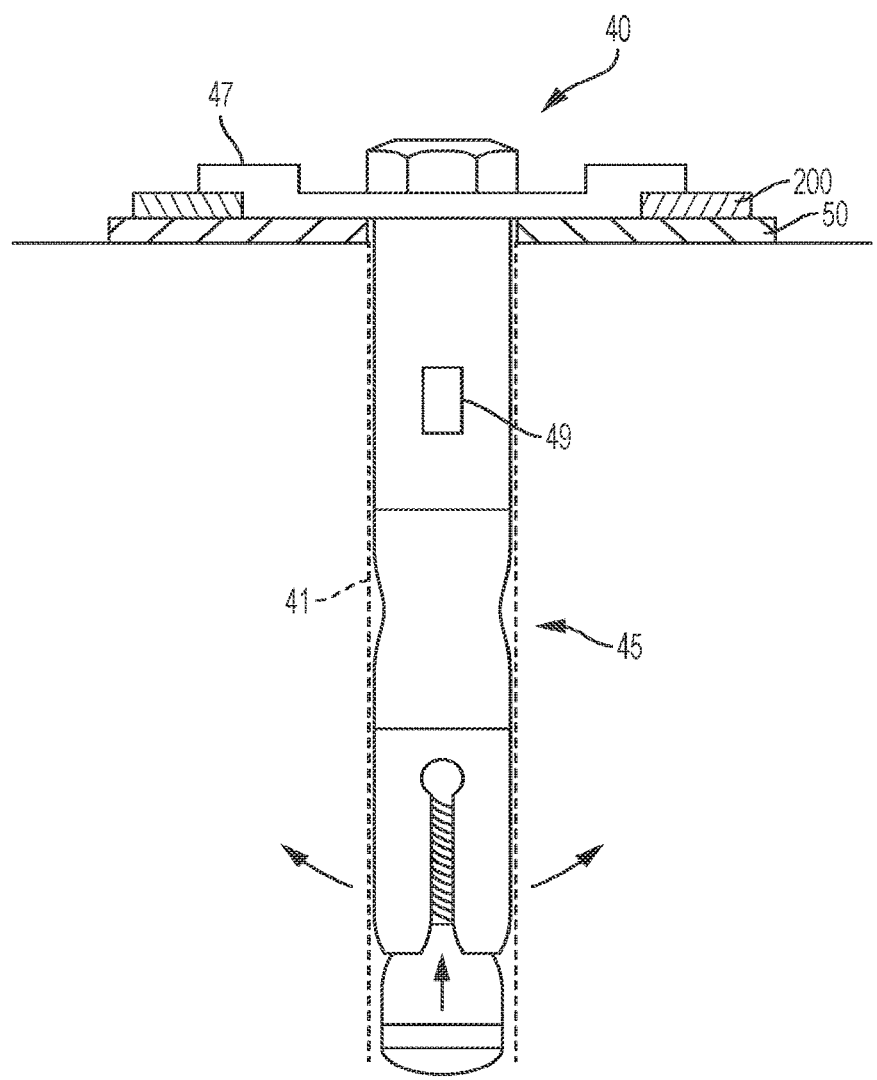
Figure 3:
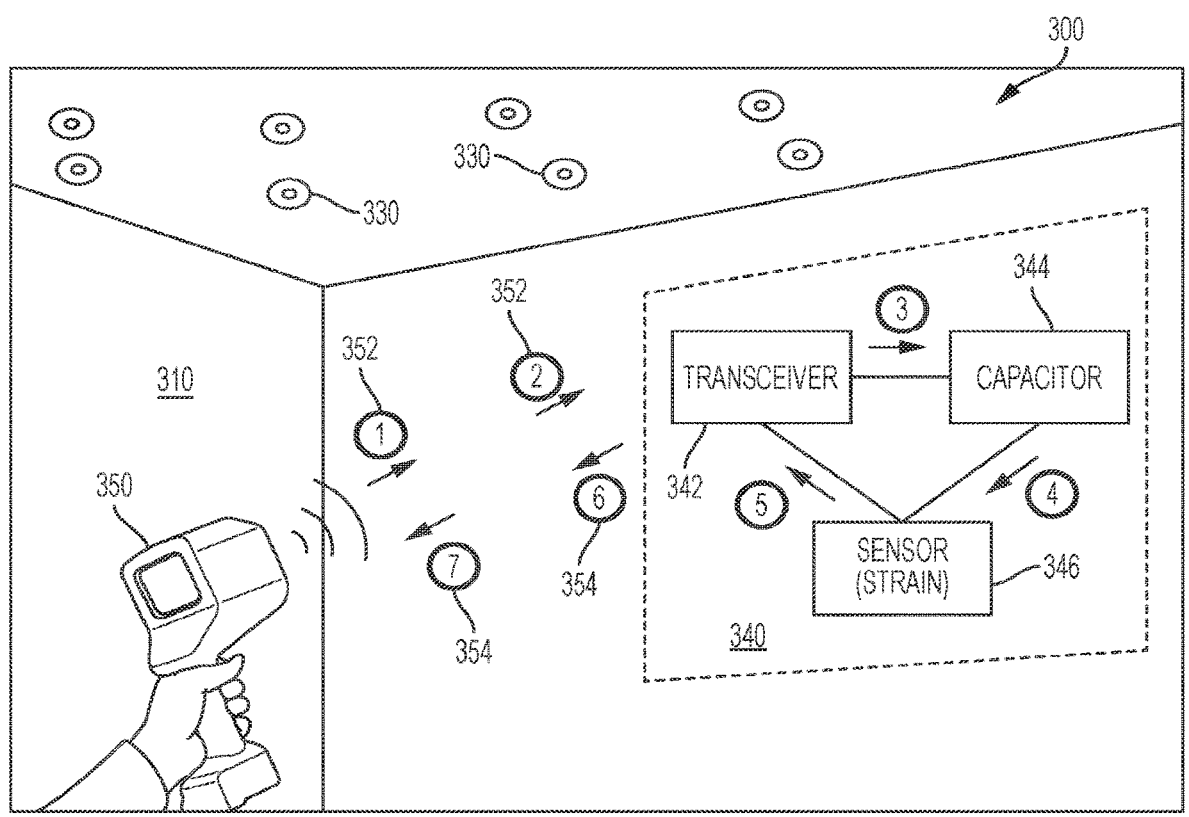
FIG. 3 shows a remote anchor information retrieval system for use with the anchor connector of FIG. 2A

FIG. 2D shows a drop-in anchor 40 for dropping into a drilled concrete hole 41. Drop-in anchor includes a shaft 45 and a head 44. Head 44 includes a flange 43 for securing a structural member 50 to the concrete 39. Shaft 45 includes female threaded wedge 46 for receiving a threaded member attached to head 44. Legs 48 of shaft 45 expand outward when head 44 is rotated to pull wedge 46 toward head 44. Expanded legs 48 engage walls of hole 41 to secure anchor 40 in hole 41. Flange 43 may include an axial extension 42 that engages and transfers load between flange 43 and the object 50 to be secured to the concrete. Shaft 45 may pass through washer 200 and flange 43 may extend over washer 200 to secure washer 200 without placing washer 200 in the load path. A sensor (e.g., strain gauge) can be disposed along the shaft. For example, a strain gauge may be disposed between legs 48 and flange 43 through which tension load will be transferred between the structure 50 and flange 43. FIG. 2E shows a similar drop-in embodiment except that flange 47 is step shaped to define a recess for receiving and securing washer 200 without placing washer 200 in the load path. FIGS. 2D and 2E disclose shaft 45 that includes a wedge fastening mechanism for securing anchor 40 in hole 41. Instead, a convention screw type fastener may be substituted instead for shaft 45. When a screw mechanism is used the sensor 49 need only be placed between the flange 43 and the portion of shaft 45 where the threads make contact with the concrete. For example, a fastener having an unthreaded portion between the threaded shaft and flange 43 is contemplated. A sensor may be positioned at the unthreaded portion.

Figure 5:
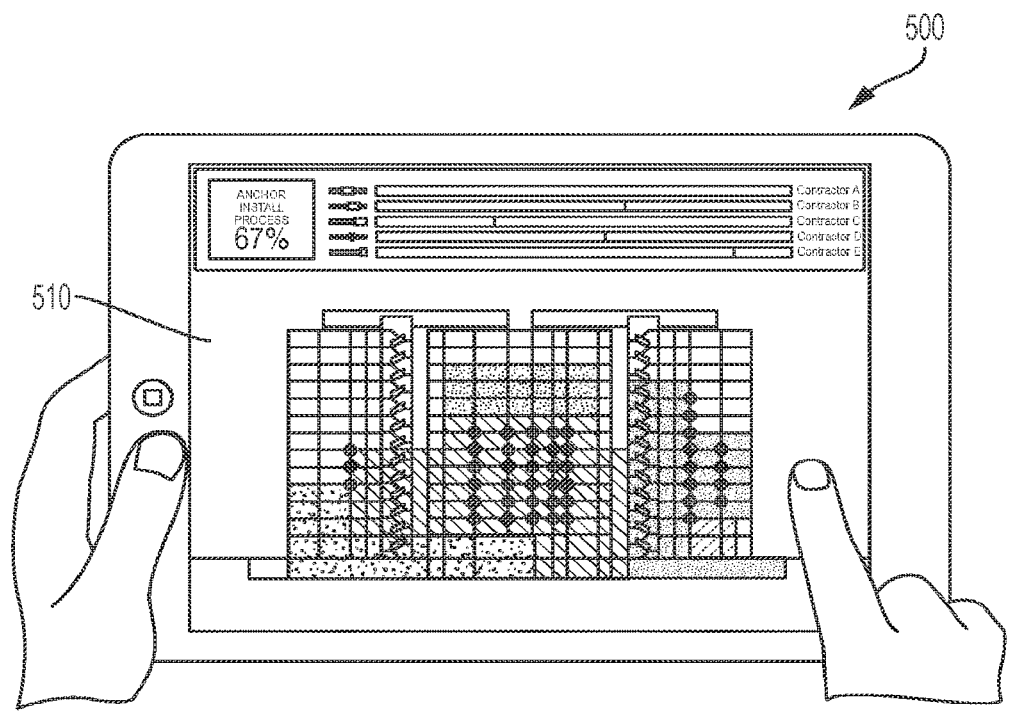
FIG. 5 shows a side view of a wireless device of the present invention displaying information sensed by the connector of FIG. 2A.

As discussed below, washer 200 is capable of wirelessly transmitting load, anchor identity and other sensed information (e.g., temperature, moisture content, wireless information from another anchor, etc.) to a remote site for processing and review. Furthermore, information from multiple connectors 100 may be wirelessly transmitted back from the various anchor elements 10, 20, 30 or connectors 100 to a remote processor or network processor for processing and generating useful information. The wireless transmission back may be directly from an anchor to the processor or to the processor from an anchor via another anchor. For example, remote electronic processors/displays may include BIM data and/or graphics for showing the actual BIM location or layout of or identity/ownership of sensed anchors and the loads on each anchor may be provided. FIG. 5 shows a possible wireless handheld display 500 (discussed in greater detail below) displaying graphics representing a facility site (e.g., construction site) and actual BIM locations of construction components (e.g., anchors) with attributes (e.g., sensed conditions) associated therewith.

While the above remote anchor condition sensing system includes both an anchor 10, 20, or 30 and a connector 100, the sensing and transmission features of an anchor system may be entirely incorporated into one and not the other. In other words, the above sensing and transmission features may be directly incorporated into an anchor 10, 20, or 30. Alternatively, a structure similar to connector 100 may be set directly in concrete (i.e., without being connected to an anchor 10, 20, 30) in much the same way anchors 10, 20, 30 are set in concrete.

For example, when connector 100 is set directly in concrete a bearing surface 130 engages the concrete to trap and anchor the connector/anchor against pull-out of the concrete. The dimensions of surface 130 may be varied to ensure adequate trapping strength. A durable, compressible, or flexible member 190 may be disposed adjacent an edge of projection 180 opposite bearing surface 130. Flex member 190 prevents concrete from approaching the space adjacent bottom surface 182. As a result, when load is applied to the threads of connector 150, connector 100 experiences strain between connector 150 and bearing surface 130. Therefore, as connector 150 is loaded, projection 180 is displaced relative to bearing surface 130 in the B direction as shown in FIG. 2B. That displacement includes a corresponding compression of flex member 190.

In an alternate embodiment, when anchors 10, 20, 30 incorporate sensing and transmission features, no connector 100 need be included. In this case, as shown in FIG. 1A, anchor 10 includes a shoulder 12 which when set in concrete resists pull-out. Anchor 10 also includes female threads 16 for receiving a threaded support rod after installation. An intermediate portion 14 is disposed between shoulder 12 and threaded member 16. Intermediate portion may include a reduced diameter portion. For example, such a reduction may facilitate the amplification of strain to make load calculation easier, more pronounced, or more accurate. A strain gauge can be disposed at the intermediate portion 14 and a smart disk 200 may be positioned on deck stop 18. As in the above embodiments, smart disk 200 receives electrical signals from anchor sensors (e.g., strain gauges, temperature sensors, pressure sensors, moisture sensors, etc.) representing the sensed condition and transmits those conditions back to a network or remote central processing station.

FIG. 3 shows a remote anchor information retrieval system 300 operating at an installation site 310 where multiple anchors 330 are installed in a facility (e.g., in a building ceiling). Each anchor 330 includes an electronic module 340 which includes a transceiver 342, a capacitor 344, and a sensor 346. System 300 also includes a transceiver 350 that may be handheld.

The system of FIG. 3 is capable of remotely retrieving a sensed condition at a remote location and includes an electronic module or onboard station 340 at the location where condition sensing is necessary and a RFID transceiver 350 remote from the location. While RFID communication is possible other wireless protocols such as Wi-Fi, UWF, Bluetooth, Zigbee, infrared light, etc. or Radio Frequency for longer distance applications may also be utilized depending on the spacing/distance of the remote objects. U.S. Provisional Patent Application No. 62/562,683 describes certain jobsite communication techniques and is incorporated herein by reference in its entirety.

The onboard station includes an onboard RFID transceiver 342 capable of receiving a wireless signal from the remote RFID transceiver 350, a sensor 346 (e.g., a strain gauge) for sensing the condition (e.g., an anchor strain) at the location and an energy storage device 344 (e.g., a capacitor) for powering sensor 346. Each of the onboard RFID transceiver 342, the sensor 346, and the energy storage device 344 are in electrical communication with each other. The electrical communication is such that the onboard RFID transceiver 342 receives energy via the wireless signal 352 transmitted from the remote RFID transceiver 350. At least some of the energy received by onboard RFID transceiver 342 is communicated to energy storage device 344 which receives and stores at least some of that energy. Sensor 346 receives and consumes at least some of that stored energy in order to sense the condition (e.g., the strain). Sensor 346 also generates a first signal representing a value of the sensed condition. Onboard RFID transceiver 342 then receives the first signal and transmits a second wireless signal 354 which is in turn received back by remote RFID transceiver 350. As mentioned, second signal 354 is received by remote transceiver 350 which could be one of multiple gateways to a network including other elements. Second signal 354 can then be processed by the remote RFID transceiver 350 or by another processor in the wireless network to determine a value of the actual condition. The actual condition value can then be displayed on the remote RFID transceiver 350 or at another device in the wireless network.

Figure 4A:
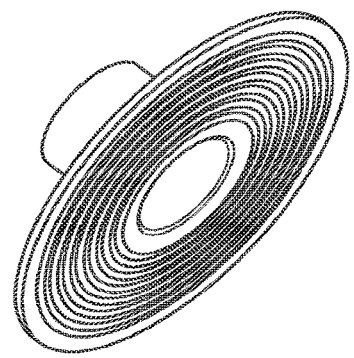
FIG. 4A shows a bottom perspective view of an embodiment of the smart disk of FIG. 2C.
Figure 4B:
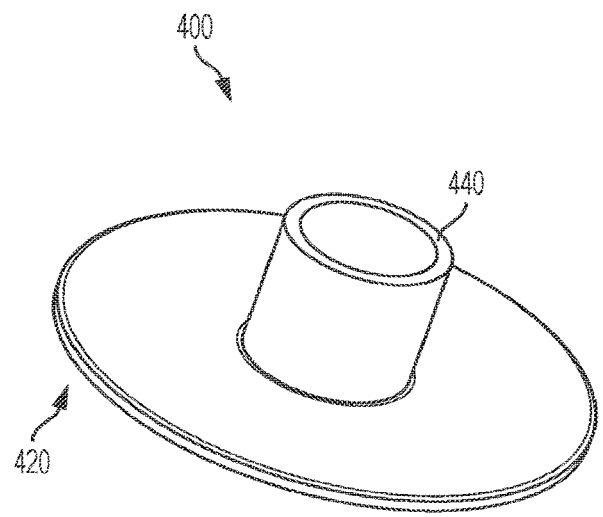
FIG. 4B shows a top perspective view of the disk of FIG. 4A.
Figure 4C:
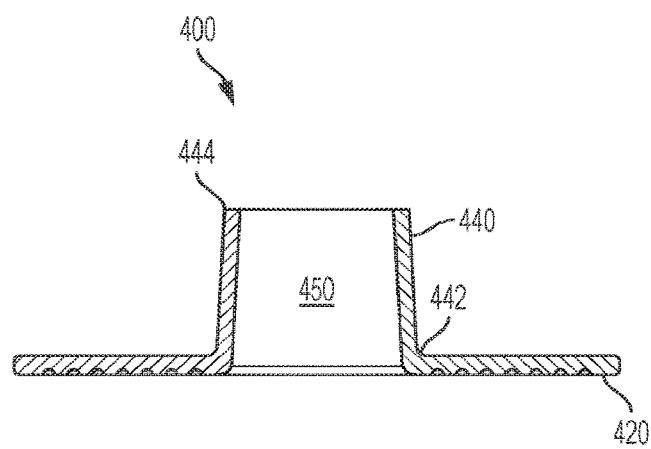
FIG. 4C shows a side cross-sectional view of the disk of FIG. 4A.

In another embodiment shown in FIG. 4A-4C, smart disk 400 is similar to smart disk 200 except that smart disk 400 includes a stud connector 440. Specifically, smart disk 400 includes a disk 420 connected to a connector 440 made of a resilient or flexible material. Connector 440 may be selectively connectable to and disconnectable from disk 420. Connector 440 also includes a central opening, is tubular and/or frustoconical in shape, and is adapted to be secured to a shaft-type structure (e.g., shaft-type anchor). Connector 440 includes a first end 422 that is connected to disk 420 and a second end 444 cantilevered from and disposed a distance from disk 442. The first end 442 of connector 440 has a diameter and the second end 444 has a second diameter that is smaller than first diameter. Therefore, disk 400 includes a central passage through both disk 420 and connector 440. Smart disk 400 is connected to studs or shafts by inserting the shaft into central passage. When the inserted shaft is slightly smaller than the diameter of the connector's first end 442 and larger than the diameter of the connector's second end 444, connector 440 will friction fit snuggly on the shaft.

FIG. 5 shows a display 500 including a wireless receiver (e.g., Wi-Fi, Bluetooth, Zigbee, infrared light, RF, etc.) in a wireless network. Display 500 can display a CAD building layout (i.e., from BIM data) showing installed smart anchors (i.e., the existence of an anchor at a particular location) to communicate a completion fraction or percentage. Display 500 can also show other sensed conditions such as temperatures, pressures, moisture content, anchor load, etc. Furthermore, installed anchors shown on displayed 500 including smart disks 200 or 400 may display other characteristics such as ownership of anchors (e.g., fire, electrical, HVAC, etc.) or type of anchors (e.g., drip in or cast in place).

The station or module 340 onboard the anchor or washer 200 may also include an LED 348 powered by the energy storage device 344. LED 348 may be energized when certain conditions are met. Furthermore, onboard RFID transceiver 342 is able to receive a wireless signal 352 from remote transceiver 350 or another device in the wireless network of a condition which, if met, would energize led 348 which could be noticed by a user from a location remote from the anchor (e.g., light up all HVAC anchors bearing more than 30 lbs load). Furthermore, various color schemes or blinking patterns on display 500 could be used to further indicate various conditions or combinations of conditions. Furthermore, if the condition is met, an image on the display 500 might be pulsed at the location of the CAD image construction site so that the user will be alerted specifically which anchors meet the condition and where they are on the construction CAD drawing.

Figure 6A:
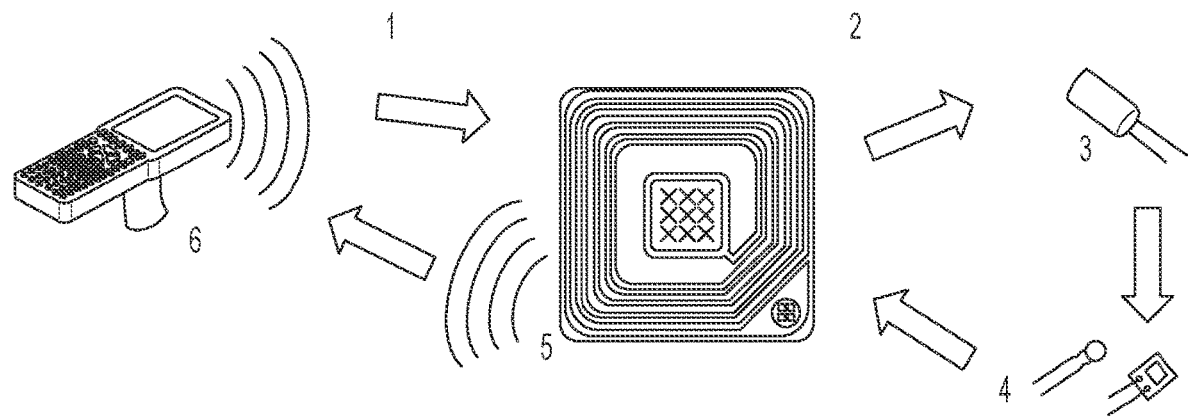
FIG. 6A shows a step diagram describing an embodiment of the present invention operating based on a new re-broadcast method.
Figure 6B:
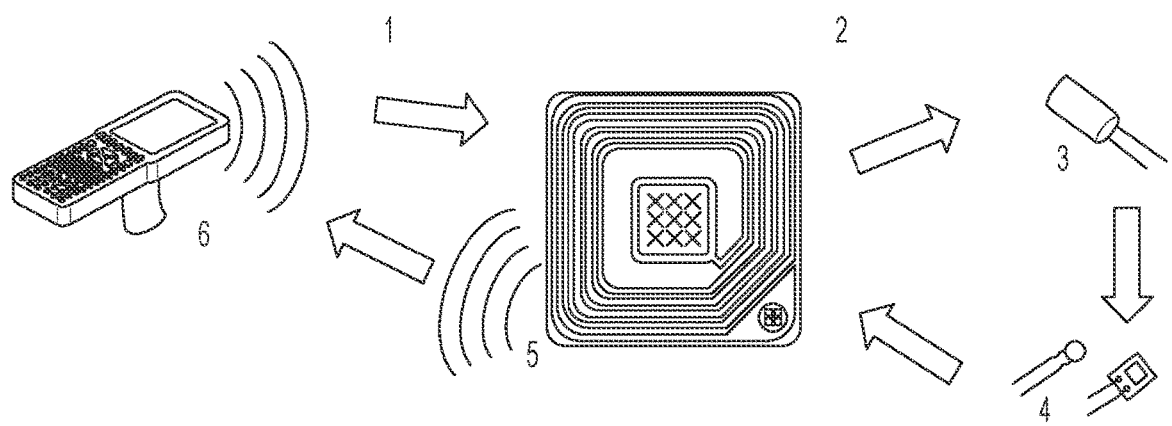
FIG. 6B shows a step diagram describing an embodiment of the present invention operating based on a new Modulation method.

FIGS. 6A and 6B illustrate the features of FIG. 3 operating based on two different electronic communication methods. First FIG. 6A illustrates the process of the system of FIG. 3 operating in a Re-Broadcast method. Here, in step 1 an RFID reader (remote transceiver 350) blasts out energy wave(s). In step 2, RFID antenna receives energy and charges up an energy storage device (e.g., a capacitor). In step 3, the capacitor stores energy until it is sufficiently charged. In step 4 when the capacitor has enough energy and is able to charge/power a circuit with a sensor and measure the sensor value (e.g., voltage drop, current, etc.). In step 5 the remaining energy from the capacitor is used to broadcast the sensor value back to the (remote transceiver 350) through the antenna. Second FIG. 6B illustrates the process of the system of FIG. 3 operating based on a Modulation Method. The Modulation method is similar to the RE-Broadcast method in steps 1-4 except that in step 5 the RFID chip's antenna modulates between absorbing state and reflecting state at a frequency modulation describing the sensor value. Furthermore, in step 6 the RFID reader (remote transceiver 350) translates modulation between reflective and absorbing states.

The present invention also contemplates a system of associating a unique anchor with a specific actual location on the job site and on a CAD building drawing. As discussed above, each anchor includes a unique wirelessly retrievable RFID identification code. That code can be associated with a specific actual 3D location on the job site either during anchor installation before the concrete is poured or after concrete curing. The process can be accomplished by pre-assigning an actual location to each uniquely coded anchor before installation begins and making sure to accurately place the anchors in their designated locations. The mapped RFID codes and locations can then be uploaded to the BIM software. This process is feasible, but could be time consuming and prone to installer error.

On the other hand, if a system included a mechanism/device (e.g., remote transceiver 350) for tracking an actual position of an item and that system was also able to superimpose that tracked actual position on CAD drawings a simpler anchor location mapping scheme than described in the previous method could be devised. Patent application Nos. 62/370,292 filed on Aug. 3, 2016; Ser. No. 14/928,470 filed on Oct. 30, 2015; 61/666,115, filed on Jun. 29, 2012, and Ser. No. 13/923,710, filed on Jun. 21, 2013, now pending are related to tool or component location, are owned by Applicant, and are each incorporated herein by reference in their entirety.

Based on this incorporated disclosure, an RFID scanning device (e.g., remote transceiver 350) could be fitted with a tag so that the actual location (e.g., 3D location or 2D and floor location (e.g., $3^{rd}$ floor)) of the scanner device 350 could be determined. When the scanner communicates with a network, a scan of an anchor while the scanner is in proximity to the anchor can automatically link a unique anchor code to an actual location by knowing the location of the scanner and reading the unique RFID code of the anchor. That data set can then be uploaded to the network to display the mapped information (e.g., superimposed on CAD building drawings). When the location of the scanner is close to multiple anchor locations as set out in the BIM design data, the system can map the uniquely scanned anchor code to the closest anchor location. Furthermore, a visible LED may light up onboard the anchor to indicate that the location of the scanner is now associated/mapped with the location of the lighted anchor. As mentioned above, the process of mapping the unique anchor code with the scanner/anchor location could be done before or after concrete placement. In any case, the process of scanning and mapping can be repeated after concrete setting to update any inaccurate information.

Moreover, the present invention contemplates a network of wireless intercommunication among onboard transceivers of multiple anchors at multiple remote locations, multiple remote transceivers, multiple displays, and multiple data processors for processing the retrieved information. Information from each anchor being associated with that anchors unique code so that each anchor's information maintains its identity as information passes among network components. Ultimately, the transmission range may be reduced to the closest adjacent anchor. A transmitting and receiving network among area building components can increase the range and performance of the wireless condition retrieval system. Furthermore, network transmitting and receiving signal boosters may be positioned permanently throughout the relevant construction site or via a temporary system (e.g., a portable system wireless networking system as disclosed in U.S. patent application No. 62/370,292).

The foregoing embodiments contemplate building construction components fitted with electronics to measure loads on and in construction components. More specifically, those loads can be applied to a construction component in various ways. For example, loads can be applied by suspending an item (e.g., a pipe) from or fastening an item to a building component (e.g., a concrete anchor). In the latter case, a threaded nut is torqued onto the threaded end of a building component (e.g., a concrete anchor bolt). A bearing surface of the nut engages a surface of the object to be secured and as the nut is tightened the building component (e.g., the concrete anchor bolt) is tensioned so that the tension of the bolt via the nut surface loads the objects surface to secure the anchor immovably to the concrete.

Figure 7A:
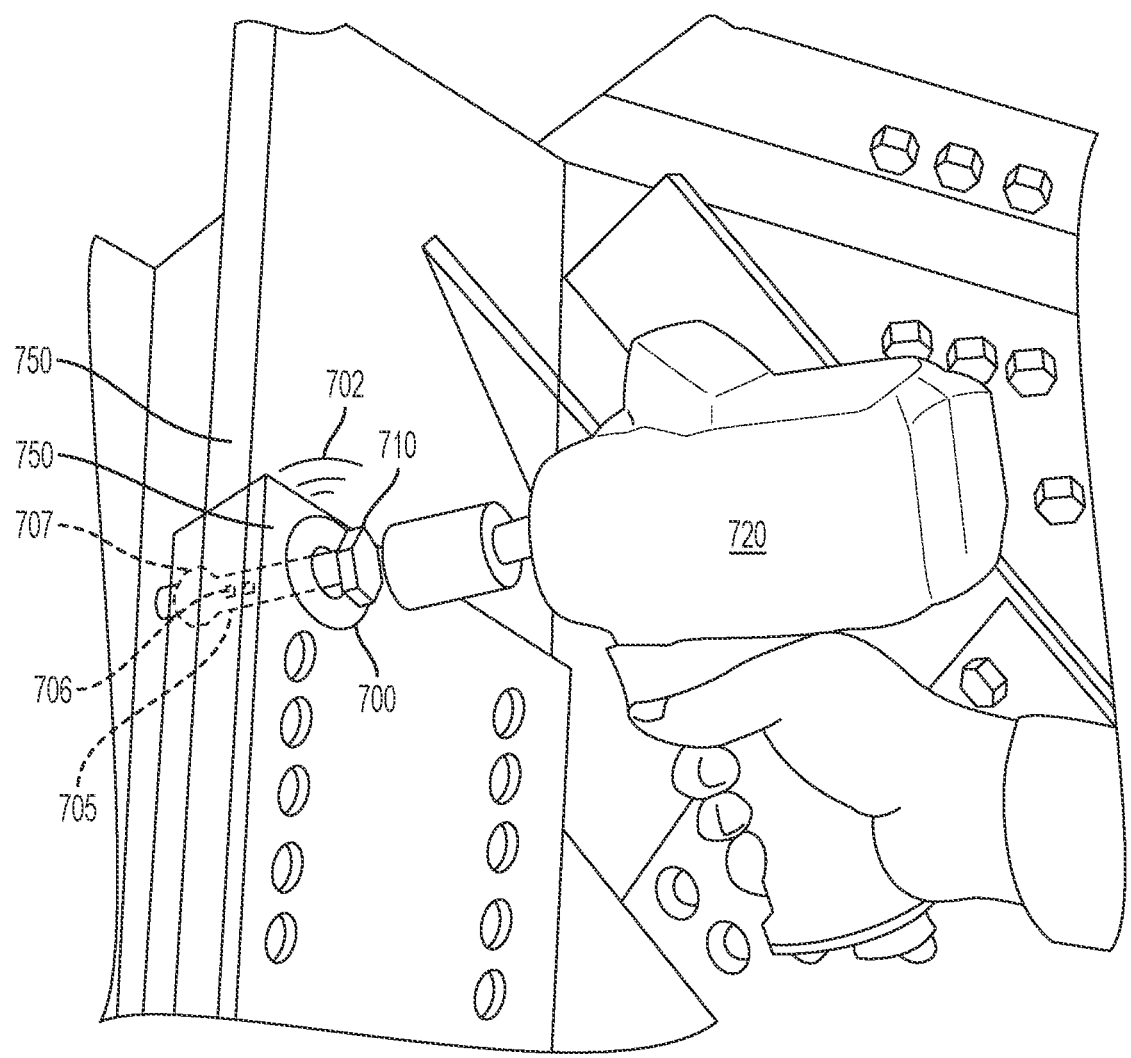
FIG. 7A shows a smart tool of the present invention being used to install a bolt clothed with a smart washer.
Figure 7B:
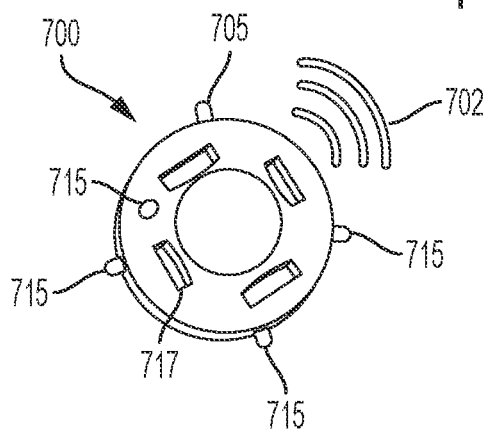
FIG. 7B shows an enlarged top perspective view of the smart washer of FIG. 7A.

As discussed herein, the construction component (e.g., the concrete anchor bolt) may include a module for housing electronics. The module may be disk shaped and the electronics may include a transceiver, an energy storage device, and a sensor. Therefore, the sensor may be a strain gauge housed in a disk shaped module such as a smart disk 200 including the same features as the washer 700 shown in FIG. 7B. This sensor in washer 700 is then able to sense and measure the tension, compression or strain developed in the concrete anchor bolt (e.g., bolts shown in FIGS. 2E and 2F). This strain is detected when washer 700 is compressed between the nut or bolt head and the object to be secured as the bolt is tightened with a torque applying device such as a torque wrench hand tool or a torque wrench power tool. Specifically, the washer is compressed in the direction of the thickness of the washer or in the direction of the longitudinal axis of the bolt around which the washer is trapped. Projections 717 may house electronic components (e.g., strain gauge). Such wireless transmission systems of smart washer 700 may be active (e.g., battery powered) or passive (e.g., able to operate with energy from outside the washer 700 or only energy from outside the washer 700). Washer 700 is then able to receive signals containing information to be stored in the washer (e.g., bolt tension, worker identity, date of completion, etc.), receive signals requesting stored information, and transmit stored and sensed information back to a remote communication device for further processing and/or display. For example, washer 700 may receive and store information related to the target bolt tension and then transmit that stored tension value back to a tool during a present or future installation or maintenance.

In a building construction component such as a concrete anchor, bolt tension is developed between one bolt end that is anchored in concrete and another end that is anchored via a nut 44 to the structural member or object 50 to be secured to the concrete pad. The smart washer 700 of the present invention may also be utilized in an application where a building component (e.g., a bolt 705) is to securely hold two or more objects 750 together (e.g., a nut 707 and bolt 705 holding two structural steel members 750 together). The reliability and security of such building construction component connections may depend on maintaining a minimum tension in bolt 705 between the bolt head 710 and the nut 707. Such building components may employ a special smart bolt 705 that includes a sensor 706 and/or may utilize a sensor in smart washer 700 of the present invention. Smart washer 700 could be located at, adjacent to, or against head 710 or nut 707 bearing surfaces between the head 710 and the building member (e.g., the first structural steel building member) or the between the nut 707 and the building member (i.e., the second structural steel building member).

The present invention contemplates smart tools 720 that may communicate directly with one or more smart washers 700 or communicate indirectly with one or more smart washers 700 via a wireless system of computers and smart washers 700. Conventional methods of installing building components securely (i.e., installation with sufficient bolt tension and no more) use hand and power tools equipped with gauges (e.g., strain gauges) for torque sensing the amount of torque being applied to a nut during the installation tightening process. The user sets the tool's torque limit manually and when the appropriate or maximum torque is reached, tightening is suspended. In the case of a torque wrench, mechanical slipping occurs so that the installer is unable to apply excess torque.

When such indirect methods are used, torque applied to the head 710 or nut 707 has to be translated/converted into tension in the bolt by estimate together with potential conversion inaccuracies. Therefore, unlike the conventional methods, the present invention smart disk 700 determines more directly (and in real time) the tension in bolt 705. Therefore, smart tools 720 that read bolt tension directly can be used to more directly, effectively and accurately install and maintain building components to the required building code tensions. Furthermore, more than one smart washer 700 may be utilized for redundancy in sensitive situations.

For example, the compression experienced by smart washer 700 may be directly and/or proportionally converted into actual bolt tension and transmitted back to the tool 720 (i.e., hand or powered tool) periodically or continuously. An installer may tighten a nut 707 periodically remembering to check a visual display on the tool that shows bolt tension to determine when to cease tightening. Alternatively, tool 720 may broadcast an audible alert to communicate to the installer that the maximum or target torques is nearing and/or reached. Furthermore a visual display such as light (e.g., and LED) on the tool or a light on or from smart washer 700 may serve as an indication that a particular bolt tension level has been or is about to be reached. Furthermore, the tool control system (sensing the target tension is reached) may automatically send a slow or stop signal to the motor to slow or stop the tool from tightening when the target bolt tension is reached. In a hand tool such as a torque wrench, a wireless signal 702 may be sent from smart washer 700 to tool 720 to trigger the mechanical slipping that prevents further torque transmission. Any combination of the above notifications to the user or tool may be used in any combination and cumulatively.

As discussed above, each smart washer 700 on a construction site may communicate information to a wireless network and/or to a computer to generate and present useful information wirelessly and remotely. For example, on a given day (e.g., inspection day) an inspector may transmit a request to a set of smart washer 700 installed bolts on a structure (e.g., a bridge structure). Each washer 700 could transmit back to the network the desired information (e.g., bolt tension, installer, moisture condition, temperature, etc.). That information may be processed and shown on a display 500 in any useful desired manner. For example, a visual display of the bolts 705 in their actual relative locations that is color coded to show bolt tensions. For example, green bolts are within acceptable tension tolerance, yellow bolts are within a second tolerance range, and red bolts are out of range (i.e., too little tension).

Furthermore, a building construction component history (e.g., a bolt history) may be maintained over the life of the structure. The history may take into consideration the data collected during each inspection and recommendations made (e.g., about maintenance, bolt replacement, etc.) based on predetermined criterion. Therefore, in a subsequent inspection, targeted bolt specific maintenance may be performed based on the collected and stored historical data.

In addition, after inspection, for example, a maintenance person equipped with one of the smart torqueing/tensioning tools 720 discussed above could send a request signal to one or a group of bolted smart washers 700 within reach. An LED 715 could retrieve the bolt tension data for each and light up on any washer 700 having an out of range tension. Bolted washers 700 out of the tension range and discovered during inspection would be visually identified for maintenance (i.e., replacing or retightening). An audible signal from the smart disk could be used to accomplish the same notification. The maintenance person can then use the smart tool 720 to tighten the bolts as described above. Furthermore, a unique bolt ID can be retrieved from the washer so that the tool automatically knows the target torque to stop at if a group of bolts have different required bolt tensions.

The hand tool could be a wrench type tool and the hand tool can be any convenient type torque driver such as an impact type driver. The power tool can be pneumatically powered or powered by an electric motor. The power tool transmitter may share the same power source with the electric motor or have a dedicated power source. The power tool may be a pistol grip type torque driver with a trigger for electrically connecting the battery to the electric motor. As discussed above the control system sending a stop signal to the electric motor or air supply valve in a pneumatic tool to end torque transmission when the target torque is reached regardless of whether the trigger is depressed.

The invention claimed is:

1. A remote building component information retrieval system for wirelessly retrieving sensed conditions from multiple remote locations comprising:
  a plurality of building components disposed at the multiple remote locations and each including;
    an onboard transceiver capable of sending and receiving a wireless signal;
    an energy storage device; and
    a sensor for sensing a condition at one of the multiple remote locations;
  wherein the onboard transceiver, the storage device, and the sensor communicate electrically with each other;

a transceiver located remote from at least one of the multiple remote locations and capable of transmitting a wireless signal to be received by at least one of the onboard transceivers of the plurality of building components;

wherein energy from the received wireless signal is stored in the energy storage device, wherein the sensor uses a portion of the stored energy from the energy storage device to sense a condition at one of the multiple remote locations, the sensor generates a first signal related to the sensed condition, and the sensor sends the first signal to the onboard transceiver, wherein the onboard transceiver transmits a second wireless signal related to the sensed condition back to the remote transceiver.

2. The remote building component information retrieval system of claim 1, wherein the remote transceiver includes a display which displays BIM data showing an actual location of sensed anchors.

3. The remote building component information retrieval system of claim 1, wherein the remote transceiver displays a value of the sensed condition.

4. The remote building component information retrieval system of claim 1, wherein the remote transceiver is handheld.

5. The remote building component information retrieval system of claim 1, wherein a protocol of the wireless retrieval of the sensed condition is via one of RFID, Wi-Fi, UWF, Bluetooth, Zigbee, and Infrared light.

6. The remote building component information retrieval system of claim 1, further including a processor wherein the processor wirelessly receives information transmitted back from the building component.

7. The remote building component information retrieval system of The remote building component information retrieval system of wherein information from multiple building components is processed by the processor for generating information.

8. The remote building component information retrieval system of claim 1, further including a wireless handleld processor for displaying graphics representing actual BIM locations of building components and sensed conditions associated with such building components.

9. The remote building component information retrieval system of claim 8, further including a wireless network including multiple receivers from multiple building components, and wherein the wireless handheld processor communicates with the network and wherein information communicated on the network is displayed superimposed on CAD building drawings.

10. The remote building component information retrieval system of claim 1, wherein the sensed condition is one of load, anchor identity, temperature, moisture content and a sensed condition from another remote building component.

11. The remote building component information retrieval system of claim 1, further including a wireless network including multiple processors each capable of receiving the second signal.

12. The remote building component information retrieval system of claim 11, wherein the second signal is processed by one of the processors in the wireless network.

13. The remote building component information retrieval system of claim 11, wherein the sensed condition is displayed on the remote transceiver or at another device in the wireless network.

14. The remote building component information retrieval system of claim 1, wherein the sensed condition is a load experienced by a suspended construction component.

15. The remote building component information retrieval system of claim 1, wherein the sensed condition is a compressive load of a bolt or concrete anchor.

16. The remote building component information retrieval system of claim 1, further including a wireless network in which onboard transceivers of the multiple building components at multiple remote locations intercommunicate among themselves.

17. The remote building component information retrieval system of claim 1, further including a wireless network in which information from each building component is associated with a building component's unique code so that an anchor's information maintains its identity as information passes among building components in the wireless network.

* * * * *